United States Patent [19]

Tahara et al.

[11] Patent Number: 4,514,573
[45] Date of Patent: Apr. 30, 1985

[54] ISOPRENYLAMINE DERIVATIVES

[75] Inventors: Yoshiyuki Tahara, Saitama; Yasuhiro Komatsu, Niiza; Hiroyasu Koyama, Ageo; Reiko Kubota, Hasuda; Teruhito Yamaguchi, Tokyo; Toshihiro Takahashi, Ohi, all of Japan

[73] Assignee: Nisshin Flour Milling Co., Ltd., Saitama, Japan

[21] Appl. No.: 377,579

[22] Filed: May 12, 1982

[30] Foreign Application Priority Data

May 18, 1981 [JP] Japan .................................. 56-76156

[51] Int. Cl.³ ..................... C07C 87/28; C07C 101/48
[52] U.S. Cl. ..................................... 564/387; 562/458; 564/211; 564/321; 564/363; 564/374; 564/384; 564/388; 564/389; 564/391

[58] Field of Search ............... 564/378, 384, 387, 389; 562/458

[56] References Cited

U.S. PATENT DOCUMENTS

| 3,541,154 | 11/1970 | Schmialek et al. | 564/509 |
| 3,801,652 | 4/1974 | Ruegg et al. | 564/509 X |
| 3,824,290 | 7/1974 | Henrick | 564/509 |
| 4,340,760 | 7/1982 | Tahara et al. | 564/509 X |

Primary Examiner—Robert V. Hines
Attorney, Agent, or Firm—Abelman, Frayne, Rezac & Schwab

[57] ABSTRACT

This invention relates to new isoprenylamine derivatives and acid addition salts thereof, which are useful for controlling virus infection of vertebrate animals.

4 Claims, No Drawings

ISOPRENYLAMINE DERIVATIVES

There are known heretofore various substances, which have been decided to have preventive or alleviative effects on diseases caused by virus whose host is a vertebrate animal, or which have been recognized to be capable of alleviating symptoms of the diseases by significantly enhancing antibody activity in the animal. Antivirotics reported so far include interferon, substances capable of inducing interferon, i.e. inducers (interferon inducers), and synthetic substances, such as amantadine hydrochloride or methisazone, which directly exert inhibitory effect on virus propagation. Interferon is glycoprotein having antiviral and antitumor activities, said glycoprotein being produced in situ by cells of a vertebrate animal when the cells are infected with virus, and has been known to be effective in therapy of infectious viral disease. Known inducers, which induce interferon in vertebrate animals through a process other than virus infection, include natural high molecular substances such as double strand ribonucleic acid of bacteriophage of a certain species, or synthetic high molecular substances such as double strand ribonucleic acid, typical of which is polyinosinic acid-polycytidylic acid, or low molecular inducers such as tirolone.

In the production of interferon, however, there is involved a problem how to carry out purification thereof, and in fact, no economical process for the production thereof has not been established yet. On the other hand, conventional interferon inducers have not been put to practical use mainly because of toxicity thereof. Synthetic antiviral agents which directly exert inhibitory effect on virus propagation, which are commercially available at present, have a rather narrow range of virus-infected diseases which are curable by administration of said agents, and thus the advent of novel synthetic activiral agents is earnestly desired. Taking such circumstances into consideration, the present inventors extensively conducted studies in finding compounds capable of producing interferon of high potency and, moreover, having antiviral activity on the biological level, and as the result they have eventually found that compounds represented by the general formula (I) and acid addition salts thereof show excellent interferon-inducing ability and, at the same time, demonstrate excellent antiviral activity even in the biological test.

Thus, the present invention is to provide a new class of an isoprenylamine derivative represented by the following general formula

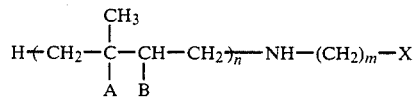

wherein n is 2 to 10, A and B are individually hydrogen atom or A and B may jointly form a single bond, and when n is 4, A and B may be a combination of the aforesaid two cases, m is 0 or an integer of 1 to 4 and when m≠0, there may be hydroxy- or phenyl-substituent on the carbons of methylene groups, and X signifies phenyl, naphthyl or diphenylmethyl, which may optionally have a nucleic substituent, and acid addition salts thereof. For the production of isoprenylamine represented by the general formula (I) and acid addition salts thereof, there may be adopted the known procedure in which isoprenyl alcohol (e.g. decaprenol, solanesol, geraniol or phytol) represented by the general formula

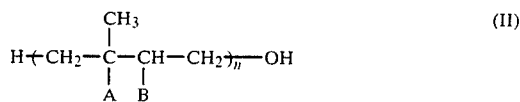

wherein n, A and B are as defined above, is first converted into a corresponding halide (e.g. decaprenyl bromide, solanesyl bromide, phytyl bromide or geranyl bromide) or arylsulfonic acid ester (e.g. decaprenyl tosylate, solanesyl tosylate, phytyl tosylate or geranyl tosylate) and the resulting halide or ester is then allowed to react in the presence or absence of a base with an amino compound represented by the general formula

wherein m and X are as defined above. This reaction is usually carried out in an organic solvent. Preferably usable as organic solvents in the reaction are common solvents such as methanol, ethanol, chloroform, isopropyl ether, ethyl acetate and the like. The reaction is carried out suitably at a temperature ranging from room temperature up to 100° C. After the completion of the reaction, a desired isoprenylamine can be produced by treating the resultant reaction liquid according to usual isolation and purification procedures such as extraction, concentration, column chromatography, crystallization and the like.

For the production of compounds of the general formula (I), there may be adopted another process in which the aforementioned halide or arylsulfonic acid ester is allowed to react with a compound represented by the general formula

wherein M represents an alkali metal atom, and m and X are as defined above, followed by saponification.

This reaction is usually carried out in non-protonic polar solvents. Preferably usable as the solvents in the reaction are tetrahydrofuran, N,N-dimethylformamide and the like. The reaction temperature to be employed is suitably from room temperature up to 100° C. The saponification is suitably carried out by heating the reaction liquid using an alcohol type solvent (e.g. methanol or ethanol) at a temperature ranging from room temperature up to 100° C. in the presence of alkali (e.g. potassium or sodium hydroxide or ammonia). After the completion of the reaction, a desired isoprenylamine can be produced by treating the reaction liquid according to usual isolation and purification procedures such as extraction, concentration, column chromatography, crystallization and the like.

An acid addition salt of the thus produced isoprenylamine derivative can be obtained by mixing said derivative in an appropriate solvent (e.g. acetone or ethyl acetate) with a desired acid to form a salt and applying such means as concentration or crystallization to the salt. The acid addition salts suitable for use as medicines include, for example, those with hydrochloric acid, acetic acid, citric, acid, fumaric acid, lactic acid and the like.

Illustrated below are preparative examples of isoprenylamine derivatives of the present invention.

PREPARATIVE EXAMPLE 1

N-(p-methoxybenzyl)decaprenylamine hydrochloride

To an ethanol solution (100 ml) containing p-methoxybenzylamine (25 g) was added dropwise with stirring an isopropyl ether solution (100 ml) containing decaprenyl bromide (30 g) at room temperature over a period of 1 hour. After the completion of the dropwise addition, the mixture was stirred at room temperature for 3 hours and then heated under reflux for 1 hour with stirring. The reaction liquid was cooled, charged with a 5% aqueous sodium hydroxide solution (100 ml) and then extracted with isopropyl ether. The extract was washed with water and saturated saline, dried over anhydrous sodium sulfate and then concentrated under reduced pressure. The concentrate (26.5 g) was treated by chromatography with a chloroform-ethyl acetate mixture over a column packed with silica gel (300 g) to obtain N-(p-methoxybenzyl)didecaprenylamine (5.3 g) from the initially eluted fraction and N-(p-methoxybenzyl)decaprenylamine (10.5 g) from the secondly eluted fraction. The oily product thus obtained was dissolved in acetone (50 ml), charged with a hydrogen chloride-ether solution to weakly acidic, and then allowed to stand in a refrigerator overnight. The crystallized mass was separated by filtration and then dried to obtain N-(p-methoxybenzyl)decaprenylamine hydrochloride (7.1 g) represented by the following formula, the measured values of physical properties of which were as shown below.

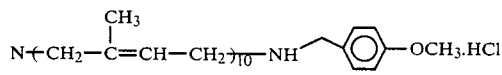

Melting point: 101.8° C.

N.M.R. (δ value in CDCl$_3$) (Free base): 7.22 (2H,d J=8 Hz), 6.80 (2H,d J=8 Hz), 4.9–5.3 (10H,br), 3.75 (3H,s), 3.68 (2H,s), 3.18 (2H,d J=7 Hz), 2.02 (36H,br), 1.60 (33H,s).

Elementary analysis (as C$_{58}$H$_{91}$NO.HCl):

|   | Calcd. | Found |
|---|---|---|
| C (%) | 81.49 | 81.45 |
| H (%) | 10.85 | 10.91 |
| N (%) | 1.64 | 1.62 |

PREPARATIVE EXAMPLE 2

N-(2,4-dimethylbenzyl)solanesylamine hydrochloride

To an ethanol solution (50 ml) containing 2,4-dimethylbenzylamine (10 g) was added dropwise with stirring an isopropyl ether solution (50 ml) containing solanesyl bromide (15 g) at room temperature over a period of 1 hour. After the completion of the dropwise addition, the mixture was further stirred at room temperature for 3 hours. The reaction liquid was cooled, charged with a 5% aqueous sodium hydroxide solution (100 ml) and then extracted with isopropyl ether. The extract was washed with water and saturated saline, dried over anhydrous sodium sulfate and then concentrated under reduced pressure. The concentrate (18.1 g) was treated by chromatography with a chloroformethyl acetate mixture over a column packed with silica gel (18.1 g). From the initially eluted faction, N-(2,4-dimethylbenzyl)disolanesylamine was obtained, and the secondly eluted fraction, N-(2,4-dimethylbenzyl)solanesylamine (7.5 g). The thus obtained N-(2,4-dimethylbenzyl)solanesylamine was dissolved in acetone (40 ml), charged with a hydrogen chloride-ether solution to weakly acidic, and then allowed to stand in a refrigerator overnight. The crystallized mass was separated by filtration and then dried to obtain N-(2,4-dimethylbenzyl)solanesylamine hydrochloride (3.9 g) represented by the following formula, the measured values of physical properties of which were as shown below.

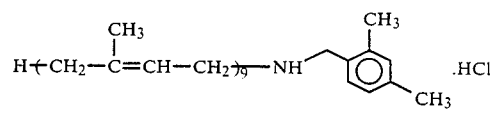

Melting point: 38.4°–40.2° C.

N.M.R. (δ value in CDCl$_3$) (Free base): 6.71–7.55 (3H,m), 4.9–5.3 (9H,br), 3.58 (2H,s), 3.16 (2H,d J=7 Hz), 2.26 (6H,s), 2.02 (32H,br), 1.60 (30H,s).

Elementary analysis (as C$_{54}$H$_{85}$N.HCl.H$_2$O):

|   | Calcd. | Found |
|---|---|---|
| C (%) | 80.80 | 80.91 |
| H (%) | 11.05 | 10.95 |
| N (%) | 1.74 | 1.71 |

PREPARATIVE EXAMPLE 3

N-(1-naphthylmethyl)decaprenylamine hydrochloride

To a pyridine solution (30 ml) containing 1-naphthylmethylamine (5.0 g) cooled on an ice bath was added dropwise with stirring trifluoroacetic anhydride (7.0 ml) over a period of 30 minutes. After the completion of the dropwise addition, the mixture was stirred while cooling for 1 hour and further stirred at room temperature overnight (about 16 hours). The reaction liquid was poured in water (200 ml) and then extracted with ethyl acetate. The extract was washed with water, 5% hydrochloric acid, 3% sodium hydrogen carbonate, water and saturated saline in that order, dried over anhydrous sodium sulfate and then concentrated under reduced pressure to obtain crude N-trifluoroacetyl-1-naphthylmethylamine (8.2 g) as yellow crystal.

To an anhydrous tetrahydrofuran solution (150 ml) containing the thus obtained crude N-trifluoroacetyl-1-naphtylmethylamine (8.2 g) while cooling with stirring was added in small portions 60% sodium hydride (1.3 g) and stirred at room temperature for 3 hours. The reaction liquid was poured in water (1 l) and then extracted with isopropyl ether. The extract was washed with water and saturated saline, dried over anhydrous sodium sulfate and then concentrated under reduced pressure. The concentrate (25.6 g) was treated by chromatography with a hexane-ethyl acetate mixture over a column packed with silica gel (300 g) to obtain N-decaprenyl-N-trifluoroacetyl-1-naphthylmethylamine (21.6 g). A mixture of an isopropyl ether solution (50 ml) containing the thus obtained N-decaprenyl-N-trifluoroacetyl-1-naphthylmethylamine (21.6 g) and a methanol solution (200 ml) containing 5% potassium hydroxide was heated at 60° C., with stirring. The reaction liquid was poured in water (1 l) and then extracted with isopropyl ether. The extract was washed with water and saturated saline, dried over anhydrous sodium sulfate and then concentrated under reduced pressure. The concentrate (19.8 g) was treated by column chromatography with chloroform-ethyl acetate mixture over a column packed with silica gel (200 g) to obtain an oily N-(1-naphthylmethyl)decaprenylamine (15.3 g). The thus obtained N-(1-naphthylmethyl)decaprenylamine was dissolved in acetone (80 ml), charged with a hydrogen chloride-ether solution to weakly acidic, and then allowed to stand at room temperature overnight. The crystallized mass was separated by filtration and then dried to obtain N-(1-naphthylmethyl)decaprenylamine hydrochloride (13.1 g) represented by the following formula, the measured values of physical properties of which were as shown below.

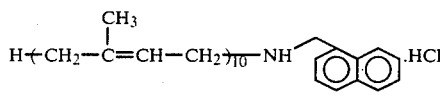

Melting point: 56.6°–61.3° C.

N.M.R. (δ value in CDCl$_3$) (Free base): 8.28–7.28 (7H,m), 4.85–5.27 (10H,br), 4.18 (2H,s), 3.33 (2H,d J=7 Hz), 2.02 (36H,br), 1.58 (33H,s).

Elementary analysis (as $C_{61}H_{91}N \cdot HCl \cdot H_2O$):

|  | Calcd. | Found |
|---|---|---|
| C (%) | 82.80 | 82.77 |
| H (%) | 10.71 | 10.53 |
| N (%) | 1.58 | 1.60 |

PREPARATIVE EXAMPLE 4

The same procedures as in Preparative Example 1 were carried out for the reaction of a halide selected from decaprenyl bromide, solanesyl bromide, geranyl bromide and phytyl bromide with an amino compound selected from p-aminobenzoic acid, p-aminosalicyclic acid, 3-phenyl-1-propylamine, p-nitrobenzylamine, p-methylbenzylamine, p-chlorobenzylamine, 3,4-dimethoxybenzylamine, amino-diphenylmethane, p-aminobenzylamine, 4-phenyl-1-butylamine, 3,4-dimethoxyphenethylamine, 4-hydroxy-3-methoxybenzylamine, m-xylenediamine, 2,3-dimethoxybenzylamine and 2-amino-1-phenylethanol, thereby to produce the below-indicated compounds, the measured values of physical properties of which were as shown in Table 1.

In the chemical structural formulas indicated hereinafter, D represents decaprenyl, S represents solanesyl, Phy represents phytyl and Ger represents geranyl.

TABLE 1

| Structural formula | Molecular formula | $n_D$/Melting point | N.M.R. (δ value in CDCl$_3$) Free base | Elementary analysis Calcd. (%) C | H | N | Found (%) C | H | N |
|---|---|---|---|---|---|---|---|---|---|
| D—NH—⟨⟩—COOH | $C_{57}H_{87}NO_2$ | 59.6–62.2° C. | 7.86(2H,d J=8Hz), 6.43(2H,d J=8Hz), 4.9–5.3(10H,br), 3.70(2H,d J=7Hz), 1.98(36H,br), 1.58(33H,s) | 83.66 | 10.72 | 1.71 | 83.71 | 10.64 | 1.67 |
| D—NH—⟨⟩(OH)—COOH | $C_{57}H_{87}NO_3$ | 54.6–56.2° C. | 7.12–7.46(3H,m), 4.9–5.3(10H,br), 3.73(2H,d J=7Hz), 2.02(36H,br), 1.60(33H,s) | 82.06 | 10.51 | 1.68 | 82.98 | 10.55 | 1.65 |
| D—NH⟨⟩·HCl | $C_{59}H_{93}N \cdot HCl \cdot 2H_2O$ | 56.0–59.4° C. | 7.18(5H,s), 4.9–5.3(10H,br), 3.27(2H,d J=7Hz), 2.63(4H,t J=7Hz), 2.02(36H,br), 1.60(35H,s) | 79.72 | 11.11 | 1.58 | 79.40 | 10.78 | 1.55 |
| D—NH⟨⟩—NO$_2$·HCl | $C_{57}H_{88}N_2O_2 \cdot HCl$ | 88.5–89.7° C. | 7.81(4H,dd), 5.22–4.82(10H,br), 3.87(2H,s), 3.22(2H,d J=7Hz), 2.00(36H,br-s), 1.59(33H,s) | 78.71 | 10.31 | 3.22 | 78.73 | 10.42 | 3.10 |
| D—NH⟨⟩—CH$_3$·HCl | $C_{58}H_{91}N \cdot HCl \cdot \frac{1}{2}H_2O$ | 98.4–101.0° C. | 7.13(4H,s), 4.9–5.3(10H,br), 3.73(2H,s), 3.22(2H,d J=7Hz), 2.33(3H,s) 2.01(36H,br), 1.60(33H,s) | 82.22 | 11.00 | 1.65 | 82.49 | 10.95 | 1.59 |
| D—NH⟨⟩—Cl·HCl | $C_{57}H_{88}NCl \cdot HCl \cdot \frac{1}{2}H_2O$ | 116–119° C. | 7.22(4H,s), 4.9–5.3(10H,br), 3.75(2H,s), 3.20(2H,d J=7Hz), 1.98(36H,br-s), 1.58(33H,s) | 78.85 | 10.45 | 1.61 | 78.77 | 10.25 | 1.57 |

TABLE 1-continued

| Structural formula | Molecular formula | nD/Melting point | N.M.R. (δ value in CDCl₃) Free base | Elementary analysis Calcd. (%) C | H | N | Found (%) C | H | N |
|---|---|---|---|---|---|---|---|---|---|
| D—NH—CH₂—C₆H₃(OCH₃)(OCH₃).HCl | C₅₉H₉₃NO₂.HCl.H₂O | 44.7–45.4° C. | 6.73–6.96(3H,m), 4.9–5.3(10H,br), 3.85(6H,s), 3.72(2H,s), 3.21(2H,d J=7Hz), 1.99(36H,br), 1.58 (33H,br-s) | 78.49 | 10.72 | 1.55 | 78.67 | 10.56 | 1.47 |
| D—NH—CH(C₆H₅)₂.HCl | C₆₃H₉₃N.HCl.½H₂O | 50.3–50.8° C. | 7.53–7.00(10H,m), 5.45–4.86(10H,br), 4.80(1H,s), 3.12(2H,d J=7Hz), 1.96(36H,br-s), 1.58(33H,s) | 83.16 | 10.52 | 1.54 | 83.17 | 10.50 | 1.52 |
| D—NH—CH₂CH₂—C₆H₄—NH₂.2HCl | C₅₈H₉₂N₂.2HCl | 148.1° C. | 6.95(2H,d J=8Hz), 6.55(2H,d J=8Hz), 4.9–5.3(10H,br), 3.20 (2H, d J=7Hz), 2.6–2.85 (4H,m), 2.00(36H,br), 1.59(33H,s) | 78.25 | 10.64 | 3.15 | 78.03 | 10.60 | 3.16 |
| D—NH—(CH₂)₃—C₆H₅.HCl | C₆₀H₉₅N.HCl.½H₂O | 53.5–55.2° C. | 7.10–7.30(5H,m), 4.9–5.3(10H,br), 3,18(2H,d J=7Hz), 2.46–2.80(4H,m), 2.02(36H,br), 1.60(37H,s) | 82.27 | 11.16 | 1.60 | 82.37 | 11.13 | 1.69 |
| D—NH—CH₂CH₂—C₆H₃(OCH₃)(OCH₃).HCl | C₆₀H₉₅NO₂.HCl.½H₂O | 69.2–72.1° C. | 6.73(3H,s), 4.9–5.3(10H,br), 3.83 (6H,s), 3.22(2H,d J=7Hz), 2.53–2.90(4H,m), 1.98(36H,br), 1.58(33H,s) | 79.37 | 10.77 | 1.54 | 79.39 | 10.79 | 1.50 |
| D—NH—CH₂—C₆H₃(OCH₃)(OH).HCl | C₅₈H₉₁NO₂.HCl.3/2H₂O | 41.7–43.1° C. | 6.75–7.30(3H,m), 4.9–5.3(10H,br), 3.83(5H,br-s), 3.40 2H,d J=7Hz), 2.00 (36H,br), 1.60(33H,s) | 77.59 | 10.66 | 1.56 | 77.28 | 10.38 | 1.52 |
| S—NH—CH₂—C₆H₃(OCH₃)(OCH₃).HCl | C₅₄H₈₅NO₂.HCl.H₂O | 57.0–64.9° C. | 6.70–6.90(3H,m), 4.9–5.3(9H,br), 3.90(6H,br-s), 3.75 (2H,s), 3.23(2H,d J=7Hz), 1.98(32H,br), 1.59(30H,s) | 77.70 | 10.62 | 1.68 | 77.55 | 10.50 | 1.63 |
| D—NH—CH₂—C₆H₄—CH₂NH₂ | C₅₈H₉₂N₂ | 30.2–31.2° C. | 7.21(4H,m), 4.9–5.3(10H,br), 3.75 (2H,s), 3.83(2H,s), 3.23(2H,d J=7Hz), 1.98 (36H,br), 1.58(33H,s) | 85.23 | 11.34 | 3.43 | 85.34 | 11.33 | 3.23 |
| D—NH—CH₂—C₆H₃(OCH₃)(OCH₃).HCl | C₅₉H₉₃NO₂.HCl.H₂O | 50.4–52.6° C. | 6.71–6.90(3H,m), 4.9–5.3(10H,br), 3.80(8H,s), 3.20 (2H,d J=7Hz), 2.02 (36H,br), 1.61(33H,s) | 79.37 | 9.71 | 1.56 | 79.48 | 9.75 | 1.48 |
| D—NH—CH(OH)—C₆H₅.HCl | C₅₈H₉₁NO.HCl.H₂O | 46.3–48.9° C. | 7.30(5H,s), 4.9–5.3(10H,br), 4.68 (1H,t J=6Hz), 3.20 (2H,d J=7Hz), 2.66(2H, t J=6Hz), 1.98(36H,br), 1.58(33H,br-s) | 79.81 | 10.85 | 1.60 | 80.03 | 10.79 | 1.49 |
| Ger—NH—CH₂—C₆H₃(OCH₃)(OCH₃).HCl | C₁₉H₂₉NO₂.HCl.½H₂O | Caramel-like | 6.71–6.96(3H,m), 5.00–5.45(2H,m), 3.83(6H,s), 3.70(2H,s), 3.23(2H,d J=7Hz), 2.03(4H,br-s), 1.63 (9H,br-s) | 65.41 | 8.95 | 4.01 | 65.38 | 8.82 | 3.93 |

TABLE 1-continued

| Structural formula | Molecular formula | $n_D$/Melting point | N.M.R. ($\delta$ value in CDCl$_3$) Free base | Elementary analysis | | | | | |
|---|---|---|---|---|---|---|---|---|---|
| | | | | Calcd. (%) | | | Found (%) | | |
| | | | | C | H | N | C | H | N |
| Phy—NH—CH$_2$—(C$_6$H$_2$)(OCH$_3$)$_2$·HCl (with OCH$_3$ substituents) | C$_{29}$H$_{51}$NO$_2$·HCl·H$_2$O | 80.0–82.6° C. | 6.70–7.00(3H,m), 5.26(1H,t J=7Hz), 3.85(6H,s), 3.70(2H,s), 3.22(2H, d J=7Hz), 0.70–2.20(36H,m) | 69.64 | 10.88 | 2.80 | 69.53 | 10.11 | 2.69 |
| S—NH—CH$_2$—(C$_6$H$_2$)(OCH$_3$)$_3$·HCl | C$_{55}$H$_{87}$NO$_3$·HCl·H$_2$O | 42.5–45.8° C. | 6.56(2H,s), 5.50–4.85(9H,br), 3.84(9H,s), 3.71(2H,s J=7Hz), 3.24(2H,d), 1.99(32H,br-s), 1.58(30H,s) | 76.39 | 10.49 | 1.62 | 76.44 | 10.29 | 1.54 |

Physiological effects of the compounds of the present invention are illustrated below in detail.

(1) Effect on mice infected with vaccinia virus

Groups, each consisting of 10 ICR female mice weighing about 15 g, were intravenously injected a dilute solution (0.1 ml) of vaccinia virus at a portion 2 cm from the base of a tail. On the 8th day after the inoculation, the number of lesions in the form of small pocks on the tail surface was counted after dyeing the tail with an ethanol solution of 1% fluorescein and 0.5% methylene blue. Each test compound suspended in a surfactant solution was administered intraperitoneally at a rate of 50 mg/kg to the mice 24 hours before inoculation of the virus, whereby antivirus activity of the test compound was evaluated in terms of inhibition of tail lesions as calculated in each test group against a group to which only the surfactant solution had been administered. The rate of tail lesion inhibition of each test compound is shown in Table 2.

TABLE 2

| Test compound (Structural formula) | Prevention from vaccinia infection (Pock inhibition rate %) |
|---|---|
| D—NH—C$_6$H$_4$—COOH | 15.0 |
| D—NH—C$_6$H$_3$(OH)—COOH | 42.9 |
| D—NH—(CH$_2$)$_3$—C$_6$H$_5$·HCl | 68.1 |
| D—NH—CH$_2$—C$_6$H$_4$—NO$_2$·HCl | 47.7 |
| D—NH—(naphthyl)·HCl | 21.6 |
| D—NH—CH$_2$—C$_6$H$_4$—CH$_3$·HCl | 44.8 |
| D—NH—CH$_2$—C$_6$H$_4$—Cl·HCl | 34.0 |
| D—NH—CH$_2$—C$_6$H$_3$(OCH$_3$)—OCH$_3$·HCl | 35.4 |
| D—NH—CH(C$_6$H$_5$)$_2$·HCl | 14.8 |
| D—NH—CH$_2$—C$_6$H$_4$—NH$_2$·2HCl | 64.4 |
| D—NH—(CH$_2$)$_3$—C$_6$H$_5$·HCl | 40.3 |
| D—NH—CH$_2$CH$_2$—C$_6$H$_3$(OCH$_3$)—OCH$_3$·HCl | 68.1 |
| D—NH—CH$_2$—C$_6$H$_3$(OCH$_3$)—OH·HCl | 67.1 |
| D—NH—CH$_2$—C$_6$H$_4$—OCH$_3$·HCl | 58.8 |
| S—NH—CH$_2$—C$_6$H$_3$(OCH$_3$)—OCH$_3$·HCl | 54.1 |
| D—NH—CH$_2$—C$_6$H$_4$—CH$_2$NH$_2$ | 91.4 |
| D—NH—CH$_2$—C$_6$H$_3$(OCH$_3$)—OCH$_3$·HCl (ortho) | 32.5 |
| D—NH—CH$_2$CH(OH)—C$_6$H$_5$·HCl | 64.4 |

TABLE 2-continued

| Test compound (Structural formula) | Prevention from vaccinia infection (Pock inhibition rate %) |
|---|---|
| Ger—NH—CH₂—C₆H₃(OCH₃)(OCH₃)·HCl | 10.0 |

(2) Effect on mice infected with influenza virus

Groups, each consisting of 10 ICR female mice weighing about 25 g were challenged by nasal inhalation of influenza virus (PR-8). Each test compound suspended in a surfactant solution was intraperitoneally administered at a rate of 50 mg/kg to the mice 24 hours before the virus infection, and 5 times every other day from the second day after the infection. The mice that survived 21 days or more after the challenge were regarded as survivors, and survival rate was obtained according to the following equation, as shown in Table 3.

$$\left[ \frac{\text{Number of survivors of test groups administered test compounds}}{10} - \frac{\text{Numbers of survivors of test groups administered only surfactant solution}}{10} \right] \times 100 = \text{Survival Rate (\%)}$$

TABLE 3

| Test compound (Structural formula) | Prevention from influenza infection (Survival rate %) |
|---|---|
| D—NH—C₆H₄—COOH | 10 |
| D—NH—C₆H₃(OH)—COOH | 50 |
| D—NH—CH₂—C₆H₄—NO₂·HCl | 40 |
| D—NH—CH₂—naphthyl·HCl | 50 |
| D—NH—CH₂—C₆H₄—CH₃·HCl | 55 |
| D—NH—CH₂—C₆H₄—Cl·HCl | 60 |
| D—NH—CH₂—C₆H₃(OCH₃)—OCH₃·HCl | 70 |
| D—NH—CH₂CH₂—C₆H₄—NH₂·2HCl | 30 |
| D—NH—CH₂CH₂—C₆H₃(OCH₃)—OCH₃·HCl | 30 |

TABLE 3-continued

| Test compound (Structural formula) | Prevention from influenza infection (Survival rate %) |
|---|---|
| D—NH—CH₂—C₆H₃(OCH₃)—OH·HCl | 60 |
| D—NH—CH₂—C₆H₄—OCH₃·HCl | 10 |
| S—NH—CH₂—C₆H₃(OCH₃)—OCH₃·HCl | 70 |
| D—NH—CH₂—C₆H₄—NH₂ | 60 |
| D—NH—CH₂—C₆H₃(OCH₃)—OCH₃·HCl | 30 |

(3) Anti-tumor activity

Groups, each consisting of 6 Balb/c male mice weighing about 20 g, were intraperitoneally administered $5 \times 10^5$ of tumor cells KN₇-8. A test compound suspended in a surfactant solution was intraperitoneally administered (each time at a rate of 30 mg/kg) to the mice 24 hours before inoculation of the tumor cells, and on the second day and the fifth day after the inoculation, totalling 3 times, and the anti-tumor activity was evaluated in terms of number of survivors on the 30th day after the inoculation. The number of survivors relative to the test compound is shown in Table 4.

TABLE 4

| Test compound (Structural formula) | Anti-tumor activity (Survivor on the 30th day) |
|---|---|
| D—NH—CH₂—C₆H₄—NH₂ | 1/6 |

(4) Toxicity

Using ddY male mice weighing 20–25 g, 50% lethal dose of each test compound when intravenously administered was obtained, the results of which are shown in Table 5.

TABLE 5

| Test compound (Structural formula) | LD₅₀ (Intravenously administered mg/kg) |
|---|---|
| D—NH—C₆H₄—COOH | 27.7 |
| D—NH—C₆H₃(OH)—COOH | 45 |
| D—NH—CH₂—C₆H₄—NO₂·HCl | >268.9 |

TABLE 5-continued

| Test compound (Structural formula) | LD$_{50}$ (Intravenously administered mg/kg) |
|---|---|
| 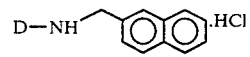 | 207.3 |
| 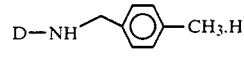 | 122.8 |
| 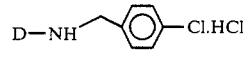 | 371.3 |
| 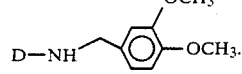 | 56.8 |
|  | 1178.7 |
| 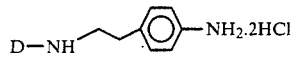 | 28 |
| 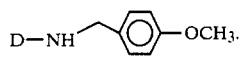 | 68 |
| 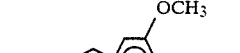 | 26 |
| 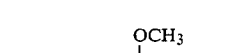 | 30 |

(5) Human interferon-inducing activity (in vitro)

Interferon was induced according to the method of Edward A. Havell et al. by treating normal diploid cells (fibroblast) originated from human being with each test compound in the form of ethanol solution diluted with PBS (−) (25 n molar suspension). Using the radioisotope microassay method of H. Ishitsuka et al., interferon was measured in terms of 3H-uridine-uptake inhibition rate. The rate of 3H-uridine-uptake inhibition of each test compound as measured is shown in Table 6.

TABLE 6

| Test compound (Structural formula) | Human interferon 3H—uridine-uptake inhibition rate % |
|---|---|
| 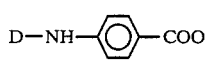 | 12.7 |
| 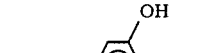 | 39.8 |
| 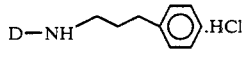 | 17.7 |
|  | 23.6 |
| 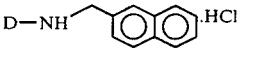 | 13.7 |
| 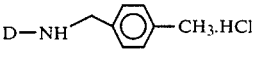 | 91.1 |
| 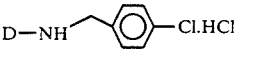 | 75.7 |
| 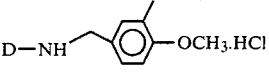 | 77.8 |
| 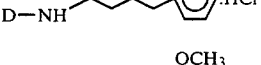 | 67.2 |
| 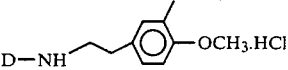 | 32.5 |
| 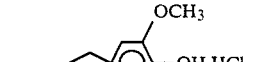 | 41.9 |
|  | 61.4 |
| 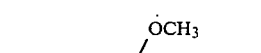 | 86.9 |
|  | 20.2 |
|  | 26.6 |
| 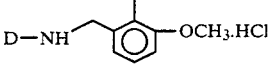 | 37.6 |
| 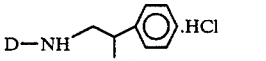 | 1.8 |
| 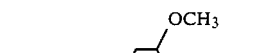 | 21.5 |

(6) Anti-vaccinia virus activity (in vitro)

Virus plaque-formation inhibition rate of each test compound was obtained by treating Vero cells originated from the kidney of African green monkey with the test compound suspension (the compound in the form of ethanol solution was suspended in Hanks culture liquid, 50 n molar concentration) and the virus diluted solution. The inhibition rate of each test compound as measured is shown in Table 7.

TABLE 7

| Test compound (Structural formula) | Anti-vaccinia virus activity Plaque inhibition rate % |
|---|---|
| S—NH—[2,6-dimethylphenyl]·HCl (CH₃, CH₃) | 9.8 |
| Phy—NH—[3,4-dimethoxyphenyl]·HCl (OCH₃, OCH₃) | 22.0 |

As is clear from the foregoing test results, the active ingredients of the present invention have interferon-inducing activity in vivo and, at the same time, are low in toxicity with showing excellent antiviral activity. In the light of the fact that the strict correlation of interferon activity with the individual antivirus activities is not always observed for the present ingredients, there is considered also a possibility that the antivirus activities of said ingredients at biological level are concerned not only in interferon but also in other defensive mechanism of host. As diseases of human being caused by virus, there are known a number of symptoms, for example, herpes-infected diseases such as herpes simplex, influenza, measles, etc. Accordingly, when the active ingredients of the present invention are used for prevention from virus infection and for the treatment of virus-infected diseases, they are administered to patients by such technique involving oral, inhalant, or the like administration as well as subcutaneous, intramuscular and intravenous injection. According to the condition of patient such as age, symptom and route by which the ingredient is administered, the active ingredient of the present invention is used in a dose of 0.5–20 mg/kg, preferably 3–5 mg/kg several times (2–4 times) per day.

The active ingredients of the present invention can be formulated into compositions for medication, for example, tablets, capsules, granules, powder, liquid preparation for oral use, eye lotions, suppositories, ointments, injections and the like.

When the present active ingredients are orally administered, they may be formulated into tablets, capsules, granules or powder. These solid preparations for oral use may contain commonly used excipients, for example, silicic anhydride, metasilicic acid, magnesium alginate, synthetic aluminum silicate, lactose, cane sugar, corn starch, microcrystalline cellulose, hydroxypropylated starch or glycine and the like; and binders, for example, gum arabic, gelatin, tragacanth, hydroxypropyl cellulose, or polyvinyl pyrrolidone; lubricants, for example, magnesium stearate, talc or silica; disintegrating agents, for example, potato starch and carboxymethyl cellulose calcium; or wetting agents, for example, polyethylene glycol, sorbitan monooleate, polyoxyethylene hydrogenated castor oil, sodium laurylsulfate and the like. In preparing soft capsules, in particular, the present active ingredients may be formulated by dissolving or suspending them in polyethylene glycol or commonly used oily substrates such as sesame oil, peanut oil, germ oil, fractionated coconut oil such as Miglyol ®, or the like. Tablet or granule preparations may be coated according to the usual method.

Liquid preparation for oral use may be in the form of aqueous or oily emulsion or syrup, or alternatively in the form of dry product which can be re-dissolved before use by means of a suitable vehicle. To these liquid preparations, there may be added commonly used additives, for example, emulsifying aids such as sorbitol syrup, methyl cellulose, gelatin hydroxyethyl cellulose and the like; or emulsifiers, for example, lecithin, sorbitan monooleate, polyoxyethylene hydrogenated castor oil, non-aqueous vehicles, for example, fractionated coconut oil, almond oil, peanut oil and the like; or antiseptics, for example, methyl p-hydroxybenzoate, propyl p-hydroxybenzoate, or sorbic acid. Further, these preparations for oral use may contain, if necessary, preservatives, stabilizers and the like additives.

In case where the present active ingredients are administered in the form of non-oral suppository, they may be formulated according to the ordinary method using oleophilic substrates such as cacao oil or Witepsol ®, or may be used in the form of rectum capsule obtained by wrapping a mixture of polyethylene glycol, sesame oil, peanut oil germ oil, fractionated coconut oil and the like in a gelatin sheet. The rectum capsule may be coated, if necessary, with waxy materials.

When the present active ingredients are used in the form of injection, they may be formulated into preparations of oil solution, emulsified solution or aqueous solution, and they may contain commonly used emulsifiers, stabilizers or the like additives.

According to the method of administration, the above-mentioned compositions can contain the present active ingredients in an amount of at least 1%, preferably 5 to 50%.

The procedure of formulating the present active ingredients into various preparations is illustrated below with reference to pharmaceutical examples.

PHARMACEUTICAL EXAMPLE 1

Hard capsule preparations for oral use

A mixture of 25 g of N-(3,4-dimethoxybenzyl)decaprenylamine hydrochloride and 7.5 g of polyoxyethylene castor oil in acetone was mixed with 25 g of silicic anhydride. After evaporation of the acetone, the mixture was mixed further with 5 g of calcium carboxymethylcellulose, 5 g of corn starch, 7.5 g of hydroxypropylcellulose and 20 g of microcrystalline cellulose, and 30 ml of water was added thereto and kneaded to give a granular mass. The mass was pelletized by means of a pelletizer (ECK pelletizer of Fuji Paudal Co., Japan) equipped with No. 24 mesh (B.S.) screen to obtain granules. The granules were dried to less than 5% moisture content and screened with No. 16 mesh (B.S.) screen. The screened granules were capsuled by means of a capsule filling machine so as to be contained in an amount of 190 mg per capsule.

PHARMACEUTICAL EXAMPLE 2

Soft capsule preparation for oral use

A homogeneous solution was prepared by mixing 50 g of N-1-(naphthylmethyl)decaprenylamine hydrochloride with 130 g of polyethylene glycol (Macrogel 400). Separately, a gelatin solution was prepared which contained 93 g of gelatin, 19 g of glycerin, 10 g of D-sorbitol, 0.4 g of ethyl p-hydroxybenzoate, 0.2 g of propyl p-hydroxybenzoate and 0.4 g of titanium oxide and which was used as a capsule film-forming agent. The previously obtained solution, together with the capsule film forming agent, was treated with a manual type flat punching machine to obtain capsules each having the contents of 180 mg.

PHARMACEUTICAL EXAMPLE 3

Injections

A mixture of 5 g of N-(3,4,5-trimethoxybenzyl)-solanesylamine hydrochloride, an appropriate amount of peanut oil and 1 g of benzyl alcohol was made a total volume of 100 cc by addition of peanut oil. The solution was portionwise poured in an amount of 1 cc under asepsis operation into an ampule which was then sealed

PHARMACEUTICAL EXAMPLE 4

Injections

A mixture of 1.0 g of N-(3,4-dimethoxybenzyl)-solanesylamine hydrochloride, 5.0 g of Nikkol HCO-60 (a trade name) (hydrogenated castor oil polyoxyethylene-60 moles-ether), 20 g of propylene glycol, 10 g of glycerol and 5.0 g of ethyl alcohol was mixed with 100 ml of distilled water and stirred. Under asepsis operation, the solution was portionwise poured in an amount of 1.4 ml into an ampule which was then sealed.

What we claim is:

1. An isoprenylamine derivative represented by the general formula

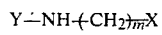

wherein Y is decaprenyl, solanesyl, or phytyl, m is zero or an integer of from 1 to 4 and when m is not zero the methylene groups are unsubstituted, or substituted by a hydroxyl or phenyl group, and X signifies substituted or unsubstituted phenyl, naphthyl or diphenylmethyl, wherein the substituents are nitro, methyl, dimethyl, chloro, mono-, di- or trimethoxy, amino, amino-methyl, carboxy, carboxy and hydroxy, or methoxy and hydroxy, and the acid addition salts thereof.

2. The compound as claimed in claim 1, which is N-(p-methoxybenzyl)decaprenylamine hydrochloride.

3. The compound as claimed in claim 1, which is N-(2,4-dimethylbenzyl)solanesylamine hydrochloride.

4. The compound as claimed in claim 1, which is N-(1-naphthylmethyl)decaprenylamine hydrochloride.

* * * * *